United States Patent [19]

Lemelson

[11] Patent Number: 5,787,885
[45] Date of Patent: Aug. 4, 1998

[54] BODY FLUID ANALYSIS SYSTEM

[76] Inventor: Jerome H. Lemelson, 930 Tahoe Blvd., Incline Village, Nev. 89451-9436

[21] Appl. No.: 322,640

[22] Filed: Oct. 13, 1994

[51] Int. Cl.$^6$ .................................................. A61B 5/00
[52] U.S. Cl. ..................... 128/632; 128/719; 128/760; 422/84
[58] Field of Search .................... 128/632, 635, 128/637, 718, 719, 730, 760–71; 422/68.1, 83, 84, 93

[56] References Cited

U.S. PATENT DOCUMENTS

| | | | |
|---|---|---|---|
| 4,830,010 | 5/1989 | Marshall | 128/719 |
| 5,299,579 | 4/1994 | Gedeon et al. | 128/718 |
| 5,386,832 | 2/1995 | Wagner et al. | 128/719 |
| 5,425,374 | 6/1995 | Ueda et al. | 128/719 |

OTHER PUBLICATIONS

Phillips, "Breath Tests in Medicine," *Scientific American*, pp. 74–79 (Jul. 1992).
"Anti-Aging News—Sniffing Out Disease," *Longevity*, p. 8 (Oct. 1994).

*Primary Examiner*—John P. Lacyk
*Attorney, Agent, or Firm*—Louis J. Hoffman

[57] ABSTRACT

A device and method for sampling and testing the breath of human beings to detect maladies in the esophagus, stomach or gastrointestinal tract by the automatic analysis of the chemical contents of the sampled breath includes a container and a microprocessor-controlled valve for allowing a select portion of the breath to enter and be stored in the container upon exhaling through an inlet to the container so as to avoid storing air which is first exhaled. A normally open pressure switch or sensor activated by the pressure of the initial flow of the breath into an inlet tube from the mouth provides a start signal for controlling an electronic timer or microprocessor, which thereafter controls the sampling operation. The apparatus also includes passageways to several collection chambers, to permit multiple samples of the same or different body fluids to be collected and analyzed with a self-contained sensor or a remote analysis system.

60 Claims, 6 Drawing Sheets

BODY FLUID ANALYSIS SYSTEM

FIELD OF THE INVENTION

This invention relates to an apparatus and method for sampling the breath of living beings and testing same to detect, by automatically analyzing the chemical contents therein, a variety of conditions and diseases of said living being such as stomach, intestinal, glandular and organ ailments, deficiencies and diseases.

BACKGROUND OF THE INVENTION

It is known in the art to collect human breath by breathing into an elongated tube through a mouthpiece wherein the breath fluid passes through one or more passageways to one or more chambers containing one or more chemicals employed to participate in or effect the analysis of the contents of the breath, which may vary based on the chemical and biological contents of the stomach and digestive tracts and glands thereof as well as organs and tissue connected thereto. Diseases and maladies are indicated and diagnosed by assaying the contents of the breath per se or by chemical or spectral analysis. The collection and analyzing equipment is large and cumbersome and is generally immobile or movable only on a cart.

It is also known to detect such diseases as gastritis, ulcers, malabsorption syndrome, cancers, and the like caused by bacteria, such as the Helicobacter pylori in the stomach or upper intestine, by measuring the level of $14CO_2$ in the breath, which is caused when a dose of urea labeled with carbon 14 released in the bacteria breaks down an area in the stomach or intestine. The $14CO_2$ is absorbed in the blood and excreted in the breath. Such breath analysis is discussed in the article by Phillips entitled "Breath Tests in Medicine," at pages 74–79 in the July 1992 issue of *Scientific American*, which is hereby incorporated by reference.

OBJECTS OF THE INVENTION

It is a primary object of this invention to provide a new and improved apparatus and method for collecting and analyzing gases and vapors, such as breath, and other body fluids under computer control using a portable device that may be transported and coupled to a testing machine, wherein the portable device is automatically operated to permit sufficient select chemicals of the sampled gas or vapor to be collected for immediate or later testing by a machine.

Another object is to provide a small portable sampling device for gases and vapors that is battery motor operated and computer or microprocessor controlled in the operation.

Another object is to provide a small portable device for sampling chemicals of body gases and vapors in concentration sufficient to permit one or more tests to be performed, such as one or more assays thereof, for diagnostic purposes.

Another object is to provide a breath sampling device that is automatically controllable by an on-board computer to allow it to sample breath and store in a segment thereof, such as a reservoir or one or more filters, sufficient quantities of chemicals of the breath to permit same to be automatically chemically analyzed in a manner to effect the diagnosis of one or more diseases or deficiencies present in the person breathing into the device.

Another object is to provide a sampling device for human breath to be tested for chemical content that is automatically controlled in its operation in a sampling cycle that is initiated by the pressure of the breath that operates a pressure switch or by an electro-optical or other type of biosensor sensing the presence of breath vapor or chemicals therein.

Another object is to provide a sampling device for human body fluids operable to collect and retain a quantity or quantities of a fluid or fluids, such as gas of the human breath, and to automatically analyze same after a select quantity of chemicals contained therein has been collected.

Another object is to provide a sampling device for human body fluid such as the breath and operable to store a plurality of samples of one or more body fluids and define the locations of a plurality of storage volumes which contain quantities of different samples of body fluid.

Another object is to provide a portable sampling device having a plurality of different storage chambers for body fluid and a storage means for a chemical reagent used in testing different quantities of such body fluid.

SUMMARY OF THE INVENTION

The instant invention employs a portable device for receiving one or more quantities of breath samples and either storing same for a period of time until the device may be transported and coupled to a testing machine or performing certain test preparations or complete test operations on the sample or samples collected or the residues thereof. The collection reservoir device maybe in the form of a plastic or glass bottle with a single reservoir, or a container with a plurality of reservoirs, each containing a strip of filter material. A fitting connected to an outlet to the container contains a one-way valve for a single inlet or a one inlet/multiple outlet valve, which may be stepped in position to allow the vapors and gases of different breaths to be stored in selected of such chambers.

In one form, the microprocessor or computer also controls a solenoid or motor to open an exhaust valve to gate initial and filtered or chemically treated breath gas from the chamber while the inlet valve is opened by the pressure of the breath or the microprocessor control signals to permit a select amount of breath fluid chemicals to be collected in the chamber and in one or more filters extending across the exhaust or outlet. When the inlet or outlet of the container (or reservoir) of the device is connected to a fluid connector of a test machine, a select amount of a select fluid of the test machine may be passed into and out of the chambers of the device to controllably flush (and clean) some of breath gas and chemicals, which may be flowed to one or more test chambers to where such residue or gas is chemically and/or biologically tested to automatically detect one or more of the chemical elements thereof. Such automatic testing and analysis may involve the computer-controlled admission of one or more select amounts of one or more chemicals or biological agents of the test site or chambers to complete or advance the test.

In another form, the test or tests to analyze the contents of the chamber or select chambers of the device may take place therein by means of a probe, sensor or sensors inserted therein or supported therein and forming part of the device, wherein chemical and/or spectral or mass spectrometry means is employed to sense and detect chemical content of the gas or residue thereof in the chamber or chambers of the device under computer control and analysis.

Other aspects of the invention will be appreciated by those skilled in the art after a reading of the detailed disclosure of the present invention below.

BRIEF DESCRIPTION OF THE DRAWINGS

The above objects and other advantages will appear from the following description and appended claims, reference being made to the accompanying drawings forming a part of the specification.

Common numerals are used in the several figures to indicate corresponding elements.

DESCRIPTION OF SPECIFIC EMBODIMENTS

Figure 1:
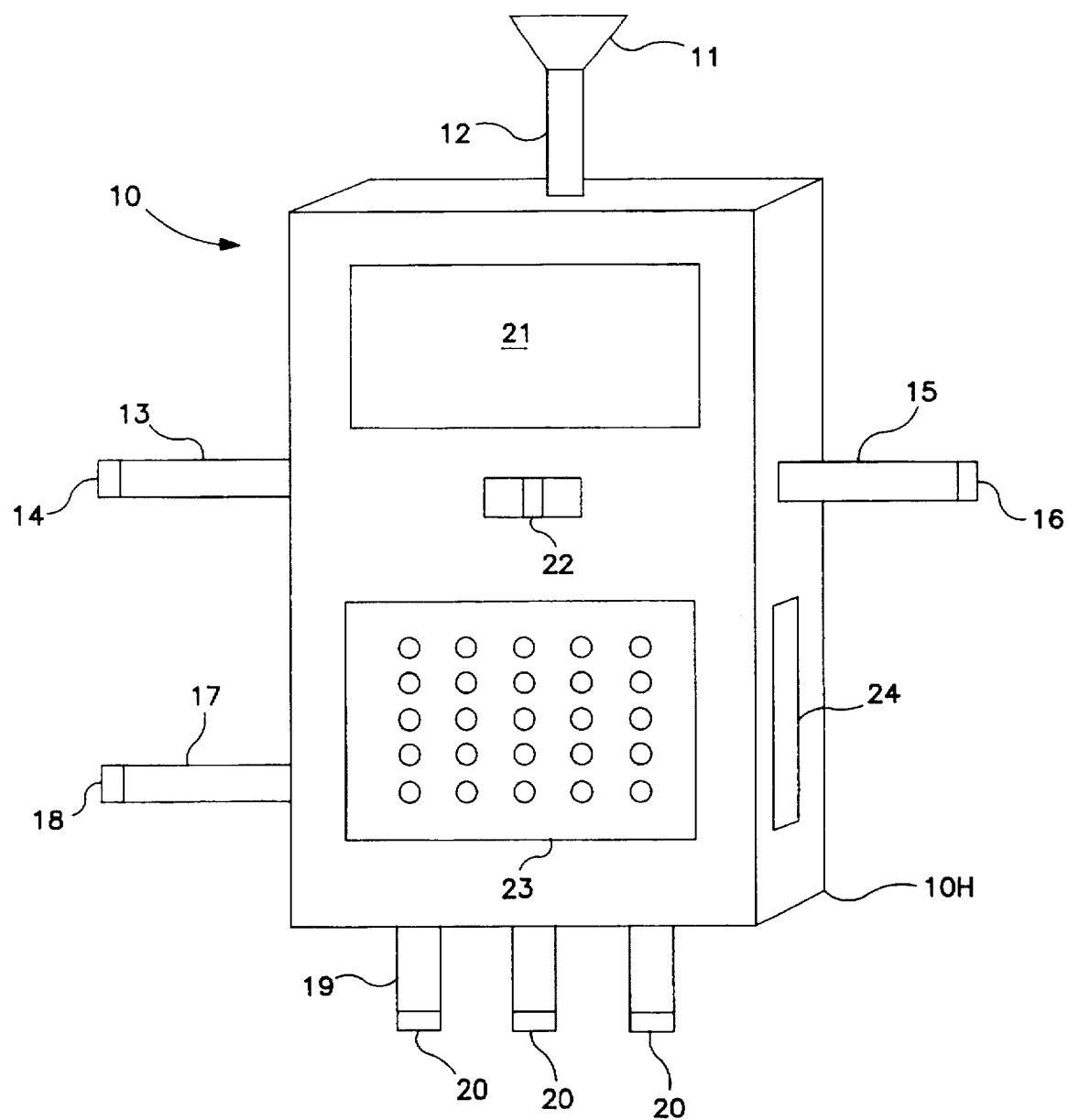
FIG. 1 is a pictorial representation of the portable breath-analysis sampling device.

The portable breath-sampling device 10 of FIG. 1 is defined by a housing 10H with a mouthpiece 11 connected thereto for collection of breath samples through the breath inlet 12 connected to the sampling device 10. Human breath samples are collected by breathing into the mouthpiece 11, inhaling air through air inlet 13 and exhaling through the exhaust or vent outlet 15 and selectable outputs 19, which may be connected to external sampling vessels or sampling filter apparatus. Air inlet 13 includes a connector 14 through which purified or otherwise preprocessed air samples may be attached to the sampling device 10 for use in breath-sample testing. Excess breath samples as well as unwanted breath samples that may occur, for example in initial breathing phases, are exhausted from device 10 through exhaust outlet 15. Exhaust outlet 15 is also equipped with a connector 16 for possible additional collection of breath samples. Breath-sampling device 10 includes internal breath-sampling liquid/water traps (not shown in FIG. 1) that require replacement of the liquid or water used in the trap to collect air samples. The trap fill/flush line 17 illustrated in FIG. 1 is used to charge such traps and to flush the liquid from the trap as appropriate and required in testing procedures.

Three selectable outlets 19 are illustrated in FIG. 1, each equipped with connectors 20 for connection to external collection vessels or filtering apparatus. While the illustration of FIG. 1 depicts three such outlets, it will be obvious that the breath-sampling device may be equipped with as few as one outlet or, in other configurations, various multiples of outlets depending on the testing requirements and the number of external vessels or filters used to capture the breath samples.

The portable breath-sampling device 10 of FIG. 1 also includes an on/off switch 22 to activate the electronic controls contained therein. The portable device 10 is battery powered, with application of power controlled by on/off switch 22. The portable, breath sampling device 10 also includes a display 21, which may, for example, be an LCD (Liquid Crystal Display) display or other display type suitable for the portable nature of the device. Also illustrated in FIG. 1 is a keyboard 23 mounted on housing 10H configured as a integral part of breath sampling device 10. Keyboard 23 may be used to enter patient identification information, test-procedure information, control parameters for proper execution of the defined breath-sampling test, breath sample identification numbers, and other information such as the identity of special gas mixture parameters connected to air inlet 13 through connector 14. Display 21 may be used to indicate to the user the appropriate test results including, for example, whether or not proper numbers of breath samples have been collected in the test procedure.

Also shown in FIG. 1 is an electrical connector 24 for connection of external electronic circuitry to portable breath-sampling device 10. Example possibilities include an external printer for printing of test results or identification stickers for collected samples. Connector 24 may also be used for transfer of sample information to external sample analysis computers, robot manipulators, or other display apparatus.

It is also possible for electrical connector 24 illustrated as part of breath-sampling device 10 in FIG. 1 to connect the sampling device 10 through appropriate telecommunication facilities to remote diagnostics and processing centers. With this capability, for example, the user of portable breath-sampling device 10 may transfer data files descriptive of the breath samples collected to a remote diagnostic center to which the breath samples themselves are also delivered via mail or other appropriate transportation means. This feature permits remote collection of breath samples, such as at the home or residence of an individual, with subsequent transfer of the breath samples and appropriate descriptive data files to a remote diagnostic and computing center for further analysis.

Figure 2:
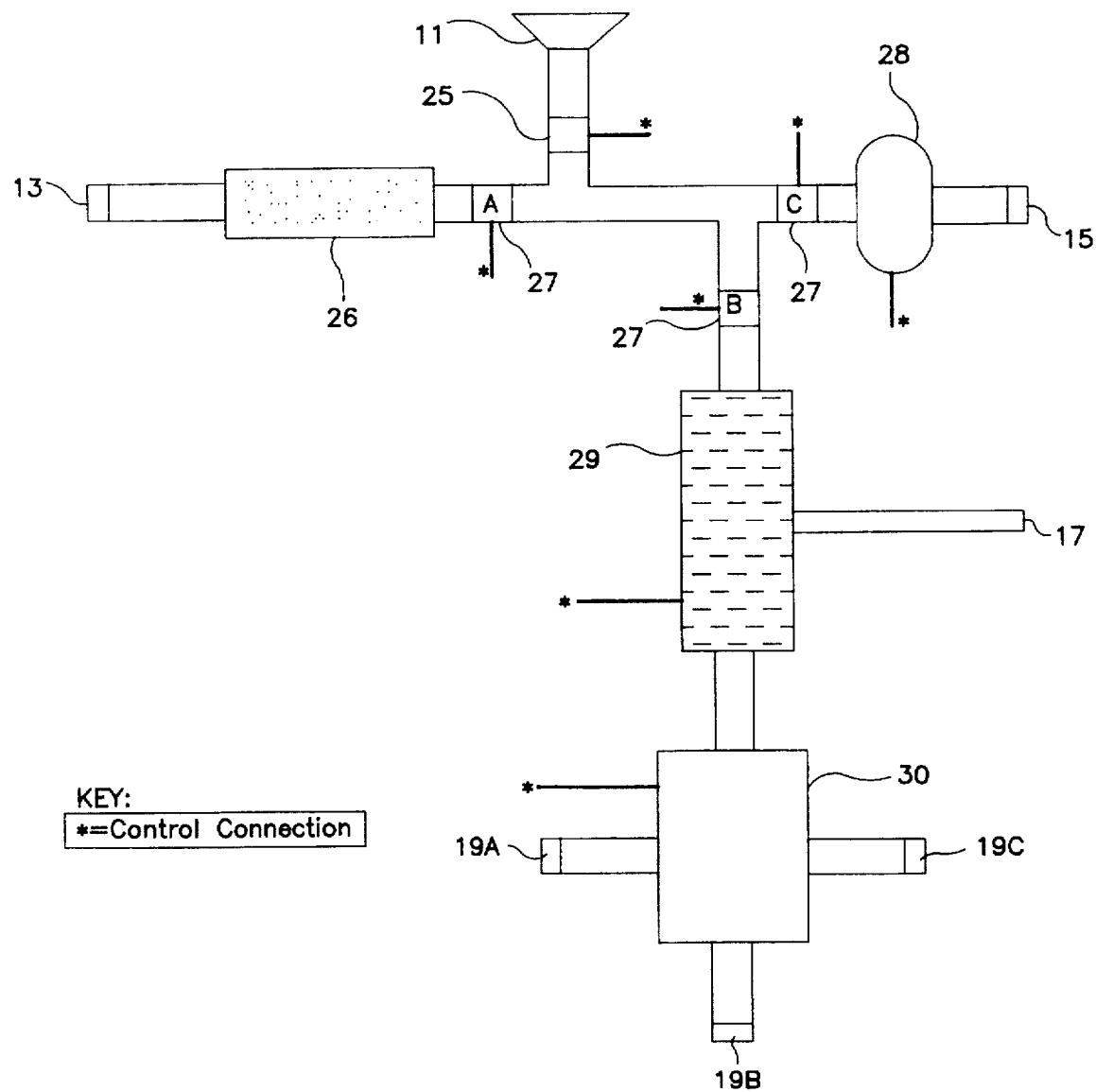
FIG. 2 illustrates internal air flow with associated filters, control valves, and air inlets and outlets from the portable breath-sampling device of FIG. 1.

FIG. 2 illustrates a schematic drawing of the internal flow of breath samples in the portable breath sampling device 10 of FIG. 1. As shown, breath samples are collected through mouthpiece 11 with breath inhaled through air inlet 13 as discussed above in connection with FIG. 1. The internal control of flow in portable device 10 is carried out using a multiplicity of pressure flow and one-way air valves properly configured to direct inhaled and exhaled breath from mouthpiece 11, insuring adequate breath sample volumes while at the same time providing sufficient air for the individual using the portable breath sampling device.

Exhaling through mouthpiece 11 activates pressure/flow start switch 25 of FIG. 2, which places the operation of portable breath sampling device 10 under the control of a microprocessor and associated control circuit further illustrated in FIG. 4 and described in more detail below. One-way valve A is configured to close when breath is being exhaled into mouthpiece 11 and to open when breath is being inhaled through mouthpiece 11. One-way valves B and C are configured to be opened when breath is exhaled and closed during the inhale cycle of normal breathing. The opened or closed state of each of valves A, B and C is monitored by the associated microprocessor control circuitry. In addition, the microprocessor control circuitry is configured to control the operation of valves B and C in a manner to provide adequate exhale air-flow paths while at the same time collecting sufficient breath samples for subsequent analysis. Initial breathing into mouthpiece 11 activates the electronic controls through switch 25. Initial activation causes one-way valve C to open and one-way valve B to close, thus preventing initial breath samples from passing to the collection outlets. Instead, initial breath samples are vented through external vent 15, as illustrated in FIG. 2.

Flow-rate sensor 28 provides to the electronic control circuitry an indication of the volume of air being exhaled by the individual using the portable breath-sampling device.

Using this information, the microprocessor control circuitry can properly manipulate one-way valves B and C during subsequent inhaling and exhaling cycles to collect the proper volume of air samples for subsequent breath analysis. By monitoring the state of one-way valve A, the microprocessor control circuitry continuously monitors the state of the breathing cycle, permitting proper operation of one-way valves B and C to insure adequate air flow while preventing inlet air from passing through valve B without first being inhaled and exhaled by the individual using the sampling device.

Also shown in FIG. 2 is a carbon air filter 26, which may be included in the overall system to filter impurities from external air being inhaled through the breath-sampling device. Other appropriate air-filtering techniques may of course be employed including, if necessary, external filters connected to air inlet 13, for air purification before the air enters the breath-sampling device. Carbon air filter 26 may be configured as removable and replaceable, to ensure proper air filtration over extended periods of use.

Also illustrated in FIG. 2 is a internal liquid/water trap 29, which may use water or other liquid to capture and wash breath samples before collection in external sampling vessels. Water trap 29 is flushed and filled through line 17, as appropriate for the proper operation of the device. The control connection to water trap 29 illustrated in FIG. 2 permits use of a small internal pump under microprocessor control to evacuate the water trap, as necessary for the proper operation of the breath sampler.

Collected breath samples are evacuated through a rotary valve 30, which is illustrated in FIG. 2 with three outlets, 19A, 19B and 19C. Rotary valve 30 operates under control of the microprocessor circuitry with successive selection of the individual outputs as appropriate for the particular breath sampling test being carried out.

Figure 3:
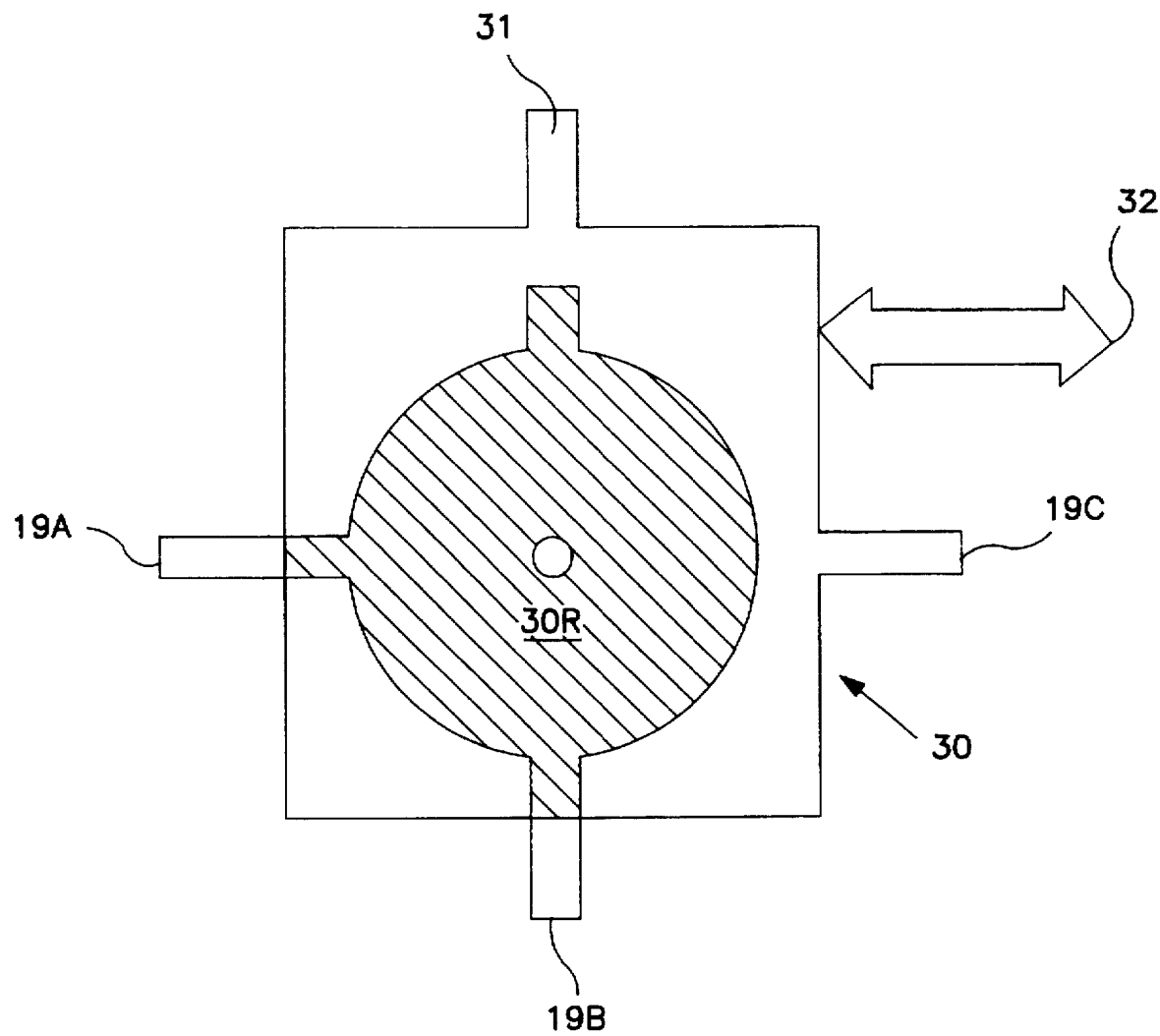
FIG. 3 is a more detailed drawing of a rotary valve useful in the portable breath-sampling device.

FIG. 3 is a more detailed drawing showing one form of rotary valve 30 employed in FIG. 2 for the selective collection of breath samples via the individual outlets 19A, 19B and 19C illustrated. Rotary valve inlet 31 is connected to water trap 29 of FIG. 2. Breath samples entering rotary 30 exit through individual valve outlets depending on the position of the internal valve rotary mechanism. As can be seen from the figure, different positions of rotary mechanism 30R will open the individual outlets one at a time. The geometry of the housing of rotary valve 30 is such that the arms of rotary mechanism 30R cannot block inlet 31 but will block at least two of outlets 19 at a time. It can also be seen from the figure that rotary mechanism 30R may be positioned to close all three selectable outlets, preventing any samples from being collected in external collection vessels connected to the outlets. In this state all incoming air samples are evacuated through the vent line 15 of FIG. 2 under control of the microprocessor circuitry.

Figure 4:
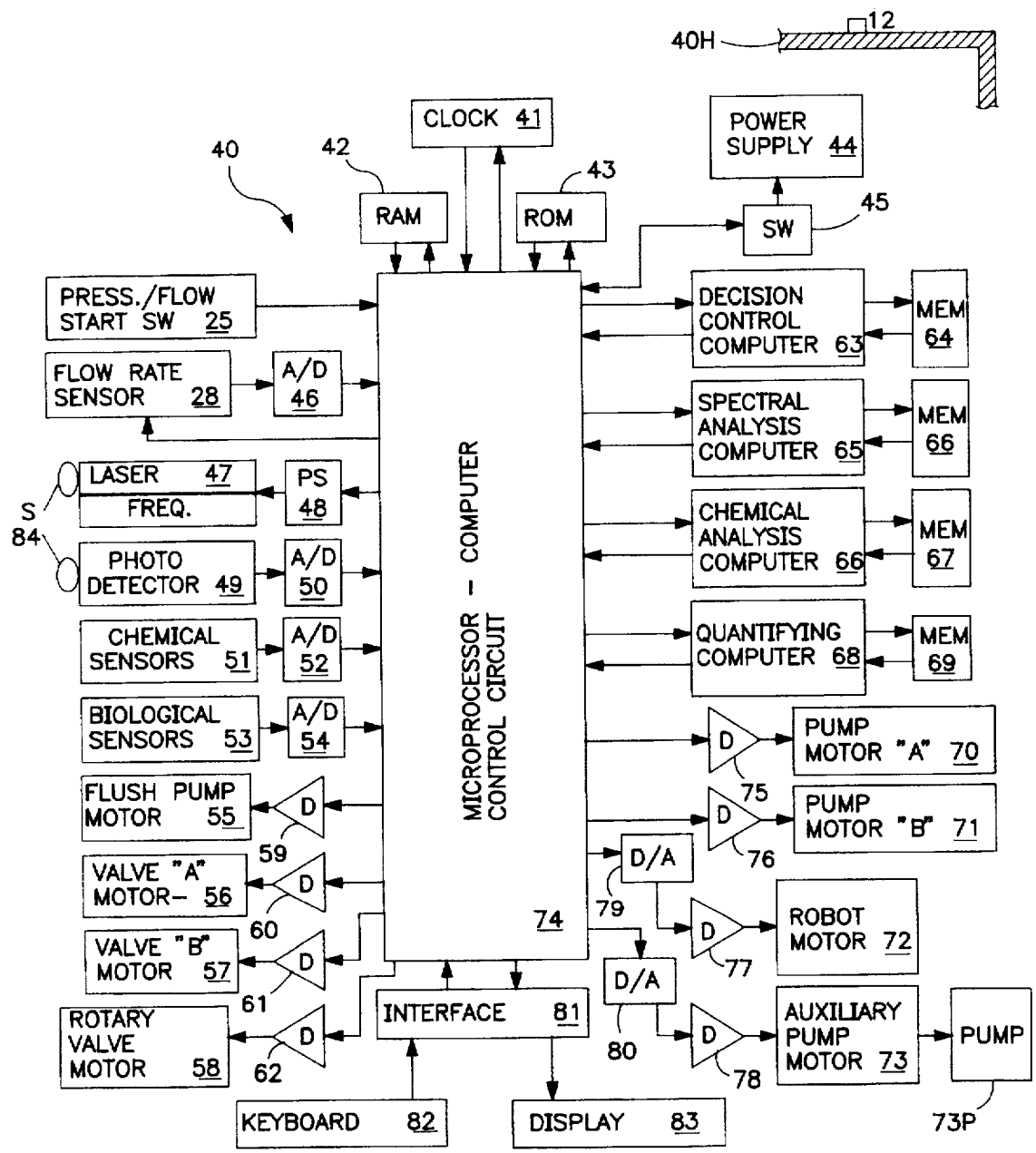
FIG. 4 illustrates in schematic diagram form electronic control circuitry for operation of the portable breath-sampling device and for subsequent analysis of collected breath samples.

FIG. 4 shows an electronic control system 40 including electronics for control of the portable collection device herein described and computer analysis circuitry for control of the analysis of collected breath samples. The portable sampling device controls are supported within a housing 40H and contain an inlet 12 for collecting fluids such as the breath of a human being.

The system 40 of FIG. 4 has a control computer or microprocessor 74 to which is connected a plurality of devices and subsystems controlled by signals generated by and passed through the microprocessor 74. A read-only memory or ROM 43 and a random access memory or RAM 42 are connected for two-way communication with microprocessor 74, the operation of which is initiated when pressure-activated start switch 25 (shown schematically in FIG. 4 and discussed above) is closed by gas pressure when a person exhales into the inlet tube 12. A manually operated switch 45 connects a power supply 44, such as a battery, to provide operating energy for microprocessor 74 and electrically operated devices connected thereto.

One of such devices is a gas or air flow sensor 28 which generates an output analog signal that varies in accordance with the rate of flow of the breath at the inlet tube. An analog-to-digital convertor 46 digitizes such analog signals providing digital signals to computer 74 for use by a quantifying computer 68.

Determining the chemical contents of the breath is effected by the use of (a) one or more chemical sensors 51 located within a chamber or container (not shown) that is located within or connected to the housing 40H, and/or (b) one or more radiation sources 47 (such as a laser) that is controlled to generate and direct one or more pulses of radiation into the collection chamber or at residue derived therefrom or from one or more filters disposed across the inlet or an outlet of the chamber. One or more photoelectric detectors 49, suitably located, detect fluorescent or reflected radiation modulated with spectral information.

One or more bio-sensors 53 may also be employed to sense biological material in the collection chamber or chambers or in one or more of the filters. The analog signals output by the sensors 49, 57 and 53 are digitized by a common analog-to-digital (A/D) converter or respective A/D converters denoted 50, 52 and 54 connected to the computer 74. A flush pump driven by a motor 55 flushes the collection chamber or chambers clean with a cleaning fluid from a reservoir in response to control signals passed to a drive 59 from computer 74. The inlet valve 56 to the collection chamber may be opened by the breath or by a solenoid or motor 60 when a control signal is passed from computer 74 to drive 60 for valve 56. An outlet valve for exhausting body fluid from the collection chamber or allowing molecules of gas and particles of biological matter to be trapped in a filter in the chamber without undue resistance to flow by the build up of gas pressure, is controlled by signals from computer 74 to open and close at select times in a test cycle.

One or more reaction chemicals are admitted to the collection chamber to react on the contents of the body fluid or breath collected therein by applying control signals from computer 74 to drives 75 and 76 which control the operations of pump motors 70 and 71, the pumps of which are connected to reservoirs of such respective chemicals to be controllably pumped thereby. Such reaction chemicals are contained in external vessels connected via connector 14 to air inlet 13 of FIG. 1 with electronic control for the pump motors supplied through external electrical connector 24 of FIG. 1.

Four subsystem computers 63, 65, 66 and 68 are shown connected to the central control computer or microprocessor 74. A spectral computer 65 receives spectral information signals generated when photodetector 49 is turned on by signals from computer 74. A chemical analysis computer 66 analyzes the information signals generated by chemical and biosensors 51 and 53. A quantifying computer 68 quantifies and generates codes indicative of the quantities of select constituents of the breath or body fluids in response to signals generated by the spectral and chemical computers 65 and 66.

Each of the computers 63, 65, 66 and 68 have respective addressable memories 64, 66, 67 and 69 that may be updated or changed with code signals generated by the selective operation of a keyboard 82 or by other command control signal generating means when it is connected to microprocessor 74 through an interface or input port 81. Signals generated by the operation of keyboard 82 or signals generated by the operation of any or selected of the computers 63, 65, 66 and 68 may also be employed to display select character information on a display screen 83, such as an LCD display or other type of electronic display.

One or more motors 72 having attendant motor drives 77 are controlled by signals received by microprocessor 74 from decision-control computer 63 to operate an integral (or external) manipulator for a sample-retaining-device, such as a filter or group of filters, to automatically remove and/or replace filters that contain sampled matter to be analyzed with new filters or filter material.

A rotary valve drive motor 58 is shown for the embodiment in which a plurality of separate storage units or chambers are provided, each of which is operable to receive and store the contents or residue of body fluid such as breath flowed through the mouthpiece tube 12 at different times. For example, samples can be taken during different times of the day, before and after meals, or after quantities of different chemicals or gases (such as radio-labeled 14C compound) are inhaled, ingested or injected. The digital control signals from decision computer 63 are converted to analog form by an analog-to-digital converter and then applied to a motor drive 62, which operates motor 58 sequentially.

In one embodiment, computers 65, 66 and 68 of system 10 may be part of a master computer that is remote from the portable unit 10 and is operably connectable thereto through an interface 81 or other means to receive coded data directly from the sensors 49, 51 and 53 or reproductions of recordings thereof from RAM 43 as processed by the computer 74.

An auxiliary pump or compressor 74 operated by a motor 73 controlled by a drive 78, which is controlled by signals from computer 74, pumps ambient air through a suitable air-purifying system (not shown), which may be separate from or part of portable device 10. Such purified air may be inhaled before tested breath is exhaled, to provide substantially uncontaminated air. In an alternate embodiment, such contamination-free air may also be provided to the subject or patient being tested from a compressed gas bottle, controlled through a valve operated by the patient or signals from computer 74.

Notation 41 refers to an electronic clock connected to computer 74 for properly controlling and timing the various operations discussed herein, such as properly opening and closing valves 56 and 57 to permit proper breath sampling and properly executing the sampling, sensing and testing operations.

Figure 5:
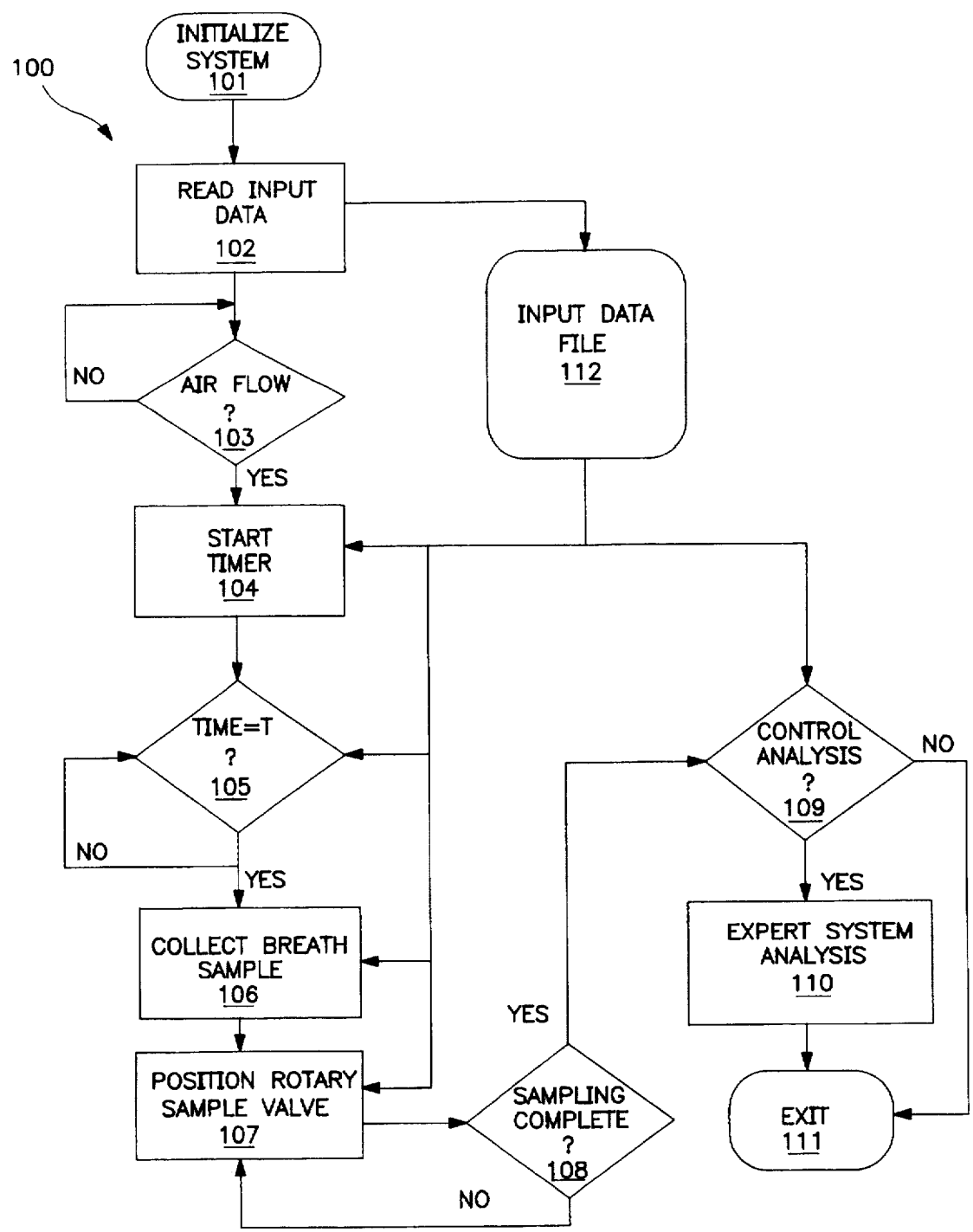
FIG. 5 is a high-level logic flow diagram for the operation of the portable breath-sampling device.

FIG. 5 illustrates a high-level flowchart for the operation of the portable breath sampling device. The system is initialized through block 101 upon activation of on/off switch 22 shown in FIG. 1. Initialization includes proper setting of the control valves 19 of FIG. 2, rotary valve 30 of FIG. 2, communication parameters for external connection through the electrical connector 24 of FIG. 1, and initialization of display 21 with appropriate information or instructions for use of the portable breath sampling device 10. After initialization, the system accepts input data (see block 102 of FIG. 5). Input data are entered through keyboard 23 (FIG. 1) and may include identification of the individual, particular test parameters, control parameters, and other test characterization data necessary for the desired breath-sampling operation. Input data are collected in an input data file 112, as illustrated in FIG. 5, for subsequent use in the internal operation of the device 10 and, as appropriate, communication with external devices. Prompt and help messages may also be generated through the input data block 102 (see FIG. 5) and displayed on LCD display 23 (FIG. 1).

Having collected necessary input data, the system next indicates via display 21 (FIG. 1) that it is ready to accept breath samples via mouthpiece 11. The microprocessor control circuitry then monitors the pressure-flow start switch 25 (FIG. 2) for the presence of air flow (see block 103 of FIG. 5). When air flow through mouthpiece 11 commences, the device starts a timer (see block 104 of FIG. 5). The timer permits initial evaluation of breath through vent 15 without passage through control valve B (FIG. 2) to collection vessels attached to outlets 19A, 19B and 19C. Thus, breath from the individual is not collected until adequately purified or otherwise prepared inlet air is inhaled through air inlet 13 in sufficient quantities and for a sufficient time to ensure that the exhaled breath has sufficient time to interact with the membranes and tissues of the individual using the breath sampling device.

That initial time delay T may be input as a test parameter during execution of block 102 (FIG. 5) and stored in input data file 112 for use in control of the sampling process. Timer block 104 utilizes the stored parameter T from the input data file 112 (or, in its absence, a default parameter) for comparison with elapsed time, as determined by dock 41 (FIG. 4) for initiation of the actual breath sampling procedure. When initial delay time T has passed (block 105 of FIG. 5), breath samples are collected by the proper operation of the one-way valves B and C during the exhale cycle, as discussed in connection with FIG. 2. Program control for proper operation of the one-way valves is indicated in the "collect breath sample" block 106 (FIG. 5). Necessary input parameters for the operation of block 106 are contained in input data file 112 and may be entered during execution of block 102 (FIG. 5). It also possible that such control parameters may be contained in permanent read only memory such as ROM 43 (FIG. 4), which are then referenced through test-identification information inputted during execution of block 102 (FIG. 5). In other words, device 10 may be configured with a number of predefined test parameters, which may be accessed from ROM 43 (FIG. 4) upon proper identification of the test to be performed through keyboard 23 (FIG. 1) during step 102 (FIG. 5).

In a similar manner, block 107 (FIG. 5) describes the control of the operation of rotary valve 30 (FIG. 2) for proper sequential sampling of breath air flow by outlet lines 19A, 19B and 19C. Once again, definition of the proper sequencing of rotary valve 30 maybe obtained from input data file 112, either inputted during execution of block 102, or through loading preconfigured and predefined data files in ROM 43 (FIG. 4). Operation of block 107 continues until all necessary sampling is completed, as indicated by test 108 (FIG. 5).

When sampling is complete, analysis of individual breath samples collected in the vessels connected to outlets 19A, 19B and 19C (FIGS. 1 and 2) may be carried out under the control of the portable breath analyzer device, as further illustrated in FIG. 5. File information from input data file 112 indicates whether or not analysis of the collected samples will be carried out under the control of the portable system or transmitted for a remote analysis system at a separate diagnostic location. As indicated above, decision control computer 63, spectral analysis computer 65, chemical analysis computer 66 and quantifying computer 68 of FIG. 4 may be configured either as an integral part of the portable breath sampling device herein disclosed or may be external to this device, as appropriate.

The actual sampling analysis is carried out by expert system analysis, indicated as block 110 of FIG. 5, which may be implemented on remote computing facilities or may be integral with the portable breath sampling device, depending on design factors such as the storage capabilities, program complexities, computational horsepower, physical size constraints and cost of unit 10. Programmed in the expert analysis system block 110 are appropriate diagnostic algorithms for analysis of the collected breath samples to ascertain the condition of the individual using the portable breath sampling device. The use of fuzzy logic and neural network computer algorithms is particularly attractive for the diagnostic algorithms. However, such techniques may not be necessary for simpler diagnostic testing. For example, in many instances, the test (block 110) may consist of a simple comparison with a set point. In other instances, the set point may be determined by a simple calculation or table look-up using data inputted by the user (block 102), e.g., the set point may vary based on the subject's age or weight. In addition, the system is sufficiently flexible to permit mere reporting of test results, which would allow bypassing block 110 entirely.

Portable analyzing device 10 may also be operable to analyze the biological or chemical contents of other body fluids, such as blood, urine, saliva, sweat or other fluids. Such fluids would be fed into one or more additional inlets (not shown) of housing 10H through one or more tubes or ducts. Such automatic analysis may be effected by the use of suitable known electro-optical or biosensors supported within housing 10H or forming part of a remote system which receives small bottles or containers of the collected body fluids. Analysis of such samples can be performed while the fluid remains in its container or after it is automatically extracted.

One or more sensors, such as biosensors, laser-operated spectrographic sensors, or other forms of sensors sense one or more characteristics of the sample or specimen collected in housing 10H and generate analog information signals, which are digitized and computer-analyzed to generate code signals. Such code signals are utilized per se or are computer analyzed along with the code signals generated in sensing other body fluids such as described above. Thus, depending on the medical information sought, device 10 may be utilized to analyze the breath of a living being per se or along with the automatic analysis of one or more other body fluids. The test results may be computer-analyzed, thereby proposing or assisting in diagnosis of a single malady, deficiency or disease or a plurality of conditions, each detected and analyzed by sensing a respective of a plurality of body fluids or by computer-analysis of a plurality of body fluids.

Plural sensing tests may also be performed on a single body fluid, as described, to detect one or more conditions. The contents of sweat may be sensed by placing an electrically energized sensor or sensors connected to the electronics of device 10 against the skin. A probe inserted in the mouth in the manner of a thermometer may sense the contents of saliva for analysis.

In a modified form of the invention, it is noted that one or more flexible or rigid tubes or portions of tubular instruments may be inserted into a body cavity, such as the mouth, anus, ear or nostril and worked or moved therethrough to position one or more fluid-collection orifices, such as one or more openings at the end or side wall of the tube, to collect gaseous or liquid samples from a select portion or portions of the body duct. In such an embodiment, when the orifices are correctly aligned, a continuous or pulsed negative pressure is applied to the interior of the tube. The sample or samples thus derives may be retained within a cavity or small chambers within the tube or tube wall for analysis when the tube is removed from the body duct. Alternatively, the samples may be immediately analyzed by means of a sensor, such as a biosensor or a plurality of such sensors located on a microelectronic chip supported within or at the end of the tube. The plurality of sampling locations may be determined automatically by controlling the timing of the opening of one or more miniature solenoids or motor-operated valves based on the positioning of the tube.

The collected fluid may be flowed through the tube passageway to a collection container for future analysis or examined directly by one or more sensors located beyond the far end of the tube while the tube is located within the body duct. Multiple samples may thus be derived while the tube is disposed at a series of locations in the body duct. Sensors, either formed from components or integrated on a microelectronic chip located within, at the operating end of, or beyond the far end of the tube, may perform such prompt analysis. In the latter case, a motorized or hand-operated pump or other means may be provided to draw the sample through the tube to the sensor. The output signals of the sensor may be immediately analyzed by a microelectronic computer, such as microchip supported at any suitable location within or adjacent to the tube. The analysis chip may be integrated on the same chip that contains the sensor. A one- or two-way light pipe containing an electro-optical sensing or viewing system may also be disposed in or extended along the tube.

Figure 6:
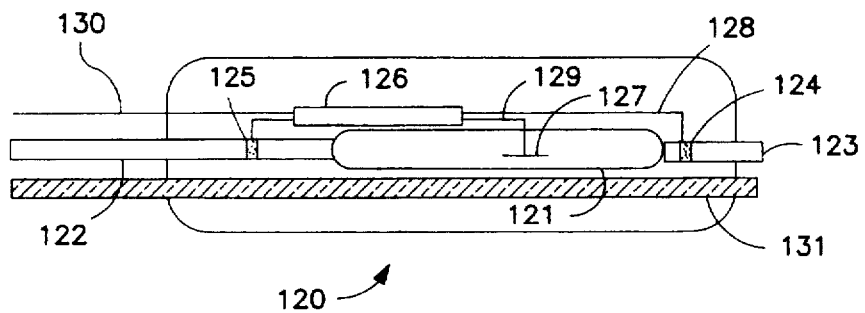
FIG. 6 illustrates a probe for body-fluid sampling.

An example of such a probe configured for body-fluid sampling by insertion into body cavities is illustrated in FIG. 6. Probe 120 is a miniature body-fluid collection and sampling device, including an internal cavity 121 for collecting body fluid samples through inlet 123. Cavity 121 is evacuated through tube 122, which in turn may be connected to various external reservoirs for body fluid analysis by external computing systems. Also shown in FIG. 6 are control valves 124 and 125, located respectively in tubes 123 and 122, which are micro-miniature, electronically operated valves under control of microcircuit controller 126. Controller 126 is a VLSI (Very Large Scale Integrated Circuit) controller built into the housing of probe 120 and used for electronic control of the valves 124 and 125 and for monitoring body-fluid sensors. Numeral 127 of FIG. 6 denotes a sensor located in collection cavity 121. Controller 126 is connected to control valve 124 through internal control communication leads 128 and to control valve 125 through similar internal wiring. Control lead 129 connects body fluid sensor 127 to controller 126. Controller 126 is also connected to external controller communication and computing devices (not shown) through communication path 130, as further illustrated in FIG. 6. With this arrangement, external control can be exercised over the probe after insertion in desired body cavities for collection of body fluid samples. Proper opening and closing of micro-valves 124 and 125 through controller 126 will enable collection of successive body fluid samples from one or more locations, as the probe 120 in properly located within the body cavity to obtain desired body fluid or body gas samples.

For example, having properly positioned probe 120 in the body cavity with valve 124 closed, valve 125 may be opened under control of controller 126. A negative pressure introduced on orifice 122 will evacuate the cavity 121. Valve 124 may then be opened, drawing in an appropriate body fluid or gas sample into the cavity 121. This may be accomplished with the valve 125 opened or closed, as appropriate for the particular test being conducted. Having completed the sampling, valve 124 may be closed and 125 opened and the cavity 121 evacuated to an external reservoir for subsequent analysis of the body fluid or gaseous samples. Alternatively, sensor 127 (FIG. 6) may be used under control of controller 126 to analyze directly body fluids or gases collected in chamber 121.

Electro-optical light pipe 131 may be a one- or two-way light pipe for sensing or viewing internal features of the body cavity into which probe 120 is inserted. External electrical connection 130, body fluid sampling tube 122 and light pipe 131 may be arranged in a common cable assembly for connection to external collection and electronic analyzing and control equipment. For example, body fluid or gaseous transmission passage 122 may be connected through connector 14 to air inlet 13 of FIG. 1, permitting probe assembly 120 to become an extension of the portable device 10. Similarly, electrical connection 130 to microprocessor controller 126 may be connected to the body fluid sampling device of FIG. 1 through electrical connector 24, permitting control of the external probe assembly 120 from the portable sampling device of FIGS. 1 and 2 described above.

Figure 7:
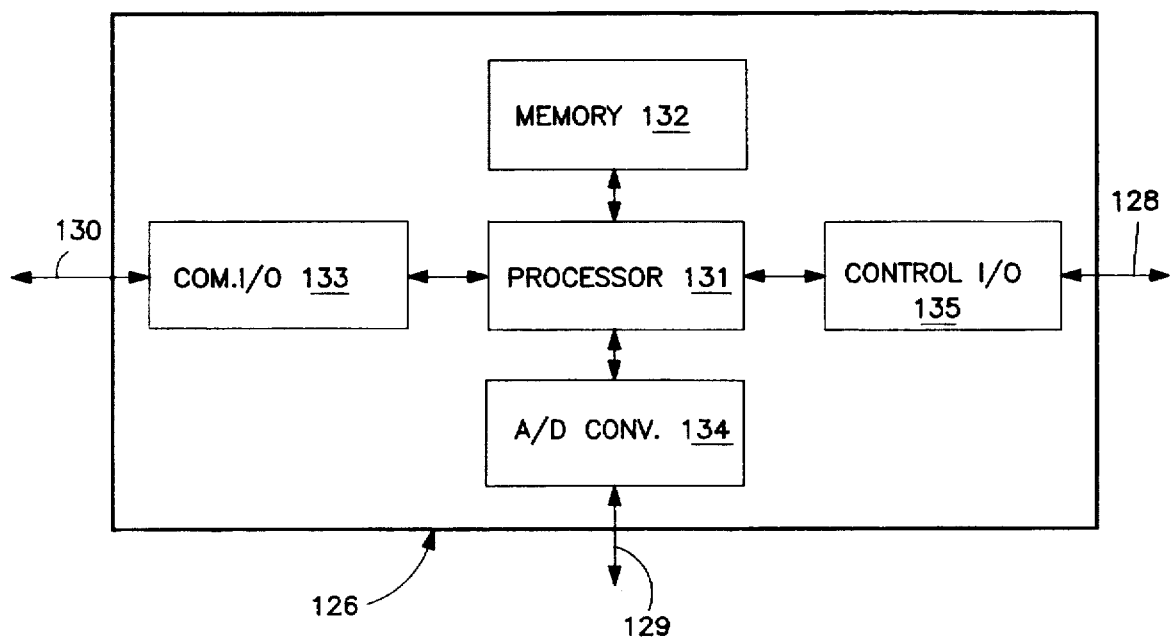
FIG. 7 illustrates internal structure of the micro-controller of FIG. 6.

FIG. 7 illustrates internal structure of the VLSI microcontroller 126 of FIG. 6. The micro-controller includes an internal processor 131 connected to memory 132. Memory 132 may be used for internal program storage and for collection and transfer of data to external devices from the probe 120. Processor 131 communicates with external communication line 130 through communication I/O port 133. In addition, an analog to digital converter 134 is used for connection via line 129 to sensors 127, as shown in FIG. 6. Internal valves 124 and 125 of FIG. 6 are controlled via control I/O port 135 (FIG. 7) via control lines 128. In some applications, actual signal processing of outputs from sensor 127 may be accomplished using processor 131 (FIG. 7) with diagnostic results communicated over line 130 (FIG. 6). The entire assembly of FIG. 7 may be integrated in a single VLSI controller chip to ensure micro-miniature implementation of the overall body cavity probe 120 of FIG. 6.

It is understood by those skilled in the art that numerous alternate forms and embodiments of the invention can be devised without departing from its spirit and scope.

What is claimed is:

1. A method for collecting and analyzing body fluid comprising:
   (a) sensing the flow of a body fluid of a living being to a first chamber of a multi-chamber collection device;
   (b) generating a control signal indicative of a predetermined parameter representative of fluid flow;
   (c) employing said control signal to initiate the select operation of a control computer;
   (d) operating said control computer thereafter in a manner to control collection of a user-selected amount of said body fluid;
   (e) causing a second sample of body fluid to flow to a second chamber of the collection device;
   (f) sensing the contents of at least one of the collected samples with a fluid sensor and generating signals; and
   (g) computer-analyzing said signals to determine the chemical composition of said sample.

2. The method of claim 1 wherein the body fluid flowing to at least one of the chambers is the breath of a human being.

3. The method of claim 2 further comprising filtering air passed to the human being, before collecting exhaled air from said human being.

4. The method of claim 2 further comprising altering the chemical composition of air passed to the human being, before collecting exhaled air from said human being.

5. The method of claim 2 further comprising passing the breath sample through a fluid trap before the sample flows to said collection device.

6. The method of claim 1 wherein the body fluid flowing to at least one of the chambers is the urine of a human being.

7. The method of claim 1 wherein the body fluid flowing to at least one of the chambers is the blood of a human being.

8. The method of claim 1 wherein the body fluid flowing to a least one of the chambers is the sweat of a human being.

9. The method of claim 1 wherein the body fluid flowing to at least one of the chambers is the lymph fluid of a human being.

10. The method of claim 1 wherein said first and second samples comprise different body fluids.

11. The method of claim 10 wherein one of said fluid samples is collected in gaseous phase and the other of said samples is collected in liquid phase.

12. The method of claim 1 further comprising causing the body fluid to flow through a filter.

13. The method of claim 1 wherein the acts in parts (d) and (g) are performed by a single, multi-function control computer.

14. The method of claim 1 wherein part (d) comprises controlling operation of a entry valve disposed at an inlet to said collection device.

15. The method of claim 14 wherein part (d) further comprises controlling operation of an exit valve disposed at an outlet from said collection device.

16. The method of claim 1 wherein part (g) is performed at a location remote from the point at which the fluid is collected.

17. The method of claim 1 wherein part (g) comprises generating signals modulated with information relating to the composition of at least a portion of said body fluid, computer analyzing said signals and generating codes representative thereof, and applying said codes to indicate a proposed diagnosis of a detected malady of the living being whose body fluid is so collected.

18. The method of claim 17
   wherein part (g) further comprises generating second signals modulated with information relating to the composition of at least a portion of said second sample, computer analyzing said second signals, and generating second codes representative thereof, and wherein said act of indicating a proposed diagnosis comprises applying said first and second codes in combination.

19. The method of claim 18 wherein said multi-chamber collection device is portable, and further comprising transporting said samples to a location remote from the point at which the fluid is collected and performing said analysis at said remote location.

20. A method for collecting and analyzing body materials comprising:
   (a) sensing the flow of a body fluid of a living being to a first chamber of a multi-chamber collection device;
   (b) generating a control signal indicative of a predetermined parameter representative of fluid flow;
   (c) employing said control signal to initiate the select operation of a control computer;
   (d) operating said control computer thereafter in a manner to control collection of a select amount of said body fluid;

(e) collecting an amount of solid material from a body duct in a second chamber of the collection device;

(f) sensing the contents of at least one of the collected amounts with a sensor and generating signals; and (f) computer-analyzing said signals to determine the chemical composition of the contents.

21. An apparatus for collecting a body fluid and analyzing its contents comprising:

(a) a housing;

(b) a fluid inlet at the exterior of said housing adapted to be disposed at an opening of a body cavity containing fluid;

(c) a inlet passageway extending from said fluid inlet into said housing;

(d) a reservoir supported by said housing and coupled to said inlet passageway;

(e) an inlet valve in said inlet passageway;

(f) a first actuator coupled to open and close said inlet valve;

(g) an exhaust passageway extending from said reservoir to the exterior of said housing;

(h) an outlet valve in said exhaust passageway;

(i) a second actuator coupled to open and close said outlet valve;

(j) a sensor positioned to detect and determine the chemical composition of body fluid in the reservoir;

(k) an electronic computing device supported by said housing, coupled to the two actuators, and coupled to the sensor; and (l) an indicating device coupled to said electronic computing device.

22. The apparatus of claim 21 wherein the electronic computing device comprises a micro-controller.

23. The apparatus of claim 21 wherein the fluid inlet is a mouthpiece.

24. The apparatus of claim 23 further comprising an air intake coupled to the mouthpiece, and an air filter positioned to filter air passing through said air intake to the mouthpiece.

25. The apparatus of claim 24 wherein the air filter comprises a fluid trap.

26. The apparatus of claim 21 wherein the reservoir comprises a plurality of chambers, the inlet passageway leads to the plurality of chambers, further comprising a valve coupling the inlet passageway to only one of the chambers at a time, and wherein the electronic computing device is coupled to and controls the valve.

27. The apparatus of claim 26 wherein the valve comprises a rotary valve.

28. An apparatus for collecting and analyzing body fluid comprising:

(a) means for sensing the flow of a body fluid of a living being through a passageway system leading to a multichamber reservoir and generating a control signal indicative of a predetermined flow of said body fluid;

(b) means for controlling the amount of said body fluid passing through a passageway leading to a first chamber;

(c) means for controlling the passage of a select amount of a second quantity of body fluid through a passageway leading to a second chamber;

(d) means for generating signals representative of the chemical composition of at least one of said body fluid amounts; and (e) means for classifying said chemical composition and reporting the determined classification.

29. The apparatus of claim 28 wherein said means (d) is further operable on said second quantity of body fluid, and wherein the body fluids in parts (b) and (c) are of different types.

30. A method for collecting and analyzing body fluid comprising:

(a) sensing the flow of a body fluid of a living being to a collection device;

(b) generating a control signal indicative of a predetermined parameter representative of fluid flow;

(c) employing said control signal to initiate the select operation of a control computer;

(d) operating said control computer thereafter in a manner to control collection of a user-selected amount of said body fluid by causing the control computer to direct operation of an entry valve disposed at an inlet to said collection device and an exit valve disposed at an outlet from said collection device;

(e) sensing the contents of said collected body fluid with a fluid sensor and generating signals; and (f) computer-analyzing said signals to determine the chemical composition of said body fluid.

31. The method of claim 30 wherein said computer: (a) first causes said exit valve to open for a select period of time while said body fluid is flowing to said collection device, (b) then causes said exit valve to close, and (c) then, some time later, causes said entry valve to close.

32. The method of claim 31 further comprising measuring the flow rate of the body fluid through the entry valve, wherein said control signal is generated when the flow exceeds a predetermined flow rate, and wherein said flow-rate measurements are used to control the timing of the operation of the computer-controlled entry and outlet valves.

33. The method of claim 30 wherein the body fluid flowing to the collection device is the breath of a human being.

34. The method of claim 33 further comprising filtering air passed to the human being, before collecting exhaled air from said human being.

35. The method of claim 33 further comprising altering the chemical composition of air passed to the human being, before collecting exhaled air from said human being.

36. The method of claim 33 further comprising passing the breath sample through a fluid trap before the sample flows to said collection device.

37. The method of claim 30 wherein the body fluid flowing to the collection device is the urine of a human being.

38. The method of claim 30 wherein the body fluid flowing to the collection device is the blood of a human being.

39. The method of claim 30 wherein the body fluid flowing to the collection device is in gaseous phase.

40. The method of claim 30 wherein the acts in parts (d) and (f) are performed by a single, multi-function control computer.

41. The method of claim 30 wherein part (f) is performed at a location remote from the point at which the fluid is collected.

42. The method of claim 30 wherein part (f) comprises generating signals modulated with information relating to the composition of at least a portion of said body fluid, computer analyzing said signals and generating codes representative thereof, and applying said codes to indicate a proposed diagnosis of a detected malady of the living being whose body fluid is so collected.

43. An apparatus for collecting a body fluid comprising:
(a) a housing;
(b) a fluid inlet at the exterior of said housing adapted to be disposed at an opening of a body cavity containing fluid;
(c) a inlet passageway extending from said fluid inlet into said housing;
(d) an inlet valve in said inlet passageway;
(e) a first actuator coupled to open and close said inlet valve;
(f) an exhaust passageway extending from said inlet passageway to the exterior of said housing;
(g) an outlet valve in said exhaust passageway;
(h) a second actuator coupled to open and close said outlet valve; and
(i) an electronic computing device supported by said housing and coupled to the two actuators.

44. The apparatus of claim 43 further comprising a plurality of chambers, wherein the inlet passageway leads to the plurality of chambers, further comprising a valve coupling the inlet passageway to only one of the chambers at a time, and wherein the electronic computing device is coupled to and controls the valve.

45. The apparatus of claim 44 wherein the valve comprises a rotary valve.

46. The apparatus of claim 43 further comprising a reservoir supported by said housing and coupled to said inlet passageway.

47. The apparatus of claim 46 wherein the reservoir comprises a plurality of chambers, the inlet passageway leads to the plurality of chambers, further comprising a valve coupling the inlet passageway to only one of the chambers at a time, and wherein the electronic computing device is coupled to and controls the valve.

48. The apparatus of claim 47 wherein the valve comprises a rotary valve.

49. The apparatus of claim 43 further comprising a sensor coupled to the electronic computing device and positioned to detect and determine the chemical composition of body fluid passed through the inlet valve, and an indicating device coupled to said electronic computing device.

50. The apparatus of claim 43 wherein the electronic computing device comprises a micro-controller.

51. The apparatus of claim 43 wherein the fluid inlet is a mouthpiece.

52. The apparatus of claim 51 further comprising an air intake coupled to the mouthpiece, and an air filter positioned to filter air passing through said air intake to the mouthpiece.

53. The apparatus of claim 52 wherein the air filter comprises a fluid trap.

54. An apparatus for collecting a body fluid comprising:
(a) a catheter sized and shaped for insertion into a body duct of a human being;
(b) a fluid inlet at the exterior of said catheter;
(c) a inlet passageway extending from said fluid inlet into said catheter;
(d) an inlet valve in said inlet passageway;
(e) a first actuator coupled to open and close said inlet valve;
(f) an exhaust passageway extending from said inlet passageway to the exterior of said catheter;
(g) an outlet valve in said exhaust passageway;
(h) a second actuator coupled to open and close said outlet valve; and
(i) an electronic computing device supported by said catheter and coupled to the two actuators.

55. The apparatus of claim 54 further comprising a reservoir coupled to said inlet passageway.

56. The apparatus of claim 55 wherein the coupling between the reservoir and the inlet passageway comprises a flexible tube.

57. The apparatus of claim 54 further comprising a sensor coupled to the electronic computing device and positioned to detect and determine the chemical composition of body fluid passed through the inlet valve.

58. The apparatus of claim 54 wherein the electronic computing device comprises a micro-controller.

59. The apparatus of claim 54 wherein the electronic computing device is coupled to an external computer.

60. The apparatus of claim 54 further comprising an endoscope sized and shaped for insertion into a body duct of a human being and supported by said catheter.

* * * * *